US00PP35879P3

(12) United States Plant Patent
Rietberg

(10) Patent No.: US PP35,879 P3
(45) Date of Patent: Jun. 25, 2024

(54) ***CHAMAECYPARIS* PLANT NAMED 'MINTA'**

(50) Latin Name: *Chamaecyparis pisifera*
Varietal Denomination: Minta

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wezep (NL)

( * ) Notice: Subject to any disclaimer, the term of this patent is extended or adjusted under 35 U.S.C. 154(b) by 0 days.

(21) Appl. No.: 18/382,142

(22) Filed: Oct. 20, 2023

(65) Prior Publication Data

US 2024/0155957 P1 May 9, 2024

(30) Foreign Application Priority Data

Nov. 3, 2022 (QZ) ..... PBR 2022/2454

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Keith O. Robinson
(74) *Attorney, Agent, or Firm* — Penny J. Aguirre

(57) ABSTRACT

A new cultivar of *Chamaecyparis* plant named 'Minta' that is characterized by its fine textured foliage, its foliage that is bluish green (minty green) in color, particularly when grown in warm temperatures, and its compact and uniformly globular plant habit.

1 Drawing Sheet

Botanical classification: *Chamaecyparis pisifera.*
Varietal denomination: 'Minta'.

CROSS REFERENCE TO A RELATED APPLICATION

This application is related to a European plant breeders' rights application filed on Nov. 3, 2022, application No. 2022/2454. The Applicant received the information for the Plant breeders' rights application directly from the Inventor.

BACKGROUND OF THE INVENTION

The present invention relates to a new and distinct cultivar of *Chamaecyparis pisifera* and will be referred to hereafter by its cultivar name, 'Minta'. 'Minta' represents a new evergreen coniferous shrub grown for landscape use.

The Inventor discovered the new cultivar in January 2020 as a naturally occurring branch mutation of *Chamaecyparis pisifera* 'Sky Blue' (not patented) that was growing in a container in a production greenhouse in Wezep, The Netherlands.

Asexual propagation of the new cultivar was first accomplished by softwood stem cuttings by the Inventor in Wezep, The Netherlands in February of 2020. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Minta' as a unique cultivar of *Chamaecyparis.*

1. 'Minta' exhibits fine textured foliage.
2. 'Minta' exhibits foliage that is bluish green (minty green) in color, particularly when grown in warm temperatures.
3. 'Minta' exhibits a compact and uniformly globular plant habit.

The parent plant of 'Minta' differs from 'Minta' in having a more vigorous and less uniform growth habit, coarsely textured foliage, and foliage that is grey-blue in color. 'Minta' can be most closely compared to *Chamaecyparis* cultivars 'Baby Blue' (not patented) and 'Boulevard' (not patented). 'Baby Blue' is similar to 'Minta' in having a relatively compact plant habit. 'Baby Blue' differs from 'Minta' in having a less uniform and less compact plant habit, coarser textured foliage, and foliage that is grey-blue in color. 'Boulevard' is similar to 'Minta' in having foliage that is bluish in color. 'Boulevard' differs from 'Minta' in having a less uniform and less compact plant habit, coarser textured foliage, and foliage that is grey-blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium, Cowell's Garden Center, Edens Plants and Creations, OZ Planten, Henrik Rietberg's Post (Linkedin), Instagram, FloraXchange, C.P.V.O., Pflanzen Springmann, Novenyfutar, Horticulture Week, Glosbe szotar, Deposit Photos, Nebih, BBKrem, BPnieuws, Goedemorgen Roos, and Floricode.

BRIEF DESCRIPTION OF THE DRAWING

The accompanying color photograph illustrates the overall appearance and distinct characteristics of the new *Chamaecyparis*. The photograph was taken of a plant 18 months in age as grown in a 10.5-cm container in a glass greenhouse in Wezep, The Netherlands. The photograph provides a view of the plant habit and foliage color of 'Minta'. The colors in the photograph are as close as possible with the photographic and printing technology utilized and the values cited in the detailed botanical description accurately describe the colors of the new cultivar.

DETAILED BOTANICAL DESCRIPTION

The following is a detailed description of plants of the new cultivar 18 months in age as grown in 9 cm circular containers in a cold story greenhouse in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen coniferous shrub.

*Plant habit*.—Compact and globular.

*Height and spread*.—An average of 12.9 cm in height and 18.4 cm in spread as an 18-month-old plant in a container, a mature plant in the landscape has been observed to reach 60 cm in height and spread to date.

*Hardiness*.—At least in U.S.D.A. Zones 3 to 11.

*Diseases and pests*.—No susceptibility or resistant to pests and diseases has been observed.

*Root description*.—Fibrous.

*Growth rate*.—Moderate.

*Root development*.—Time for root initiation is an average of 3 months from softwood cuttings in winter, time to produce a fully rooted cutting is an average of 9 months.

*Propagation*.—Softwood stem cuttings.

Stem description:

*Shape*.—Rounded.

*Stem size*.—8.4 cm in length and 2 mm in diameter.

*Stem surface*.—Glabrous, slightly glossy and smooth.

*Branching*.—Per plant; main 6, lateral 28.

*Branch arrangement*.—Alternate.

*Branch aspect*.—Average angle of 50°.

*Internode length*.—8 mm in length.

*Stem color*.—Young stems; 144B, mature stems; 145B, older wood and bark; 166B and 200D.

Foliage description:

*Leaf arrangement*.—Opposite, whorled.

*Leaf shape*.—Thinly oblanceolate to linear, slightly carinate.

*Leaf division*.—Simple.

*Leaf base*.—Decurrent.

*Leaf apex*.—Apiculate, not sharp to the touch.

*Leaf venation*.—Not visible.

*Leaf margins*.—Entire.

*Leaf surface*.—Both surfaces smooth, glabrous and matte.

*Leaf color*.—Young; upper surface 143B, lower surface 143C, mature upper surface 137D, mature lower surface 144B, 2 stomatal bands on upper and lower surfaces, on upper surface stomatal bands moderately conspicuous, 190D in color, on lower surface stomatal bands conspicuous, 130D and 190D in color.

*Leaf aspect*.—Held in an average angle of 50° to lateral branch.

*Leaf fragrance*.—Moderate fragrance when crushed, typical for *Chamaecyparis*.

*Leaf size*.—An average of 6 mm in length and 1 mm in width.

*Leaf quantity*.—An average of 500 scale-like leaves per branch.

Cone description: No cones have been observed to date.

It is claimed:

1. A new and distinct cultivar of *Chamaecyparis* plant named 'Minta' substantially as herein illustrated and described.

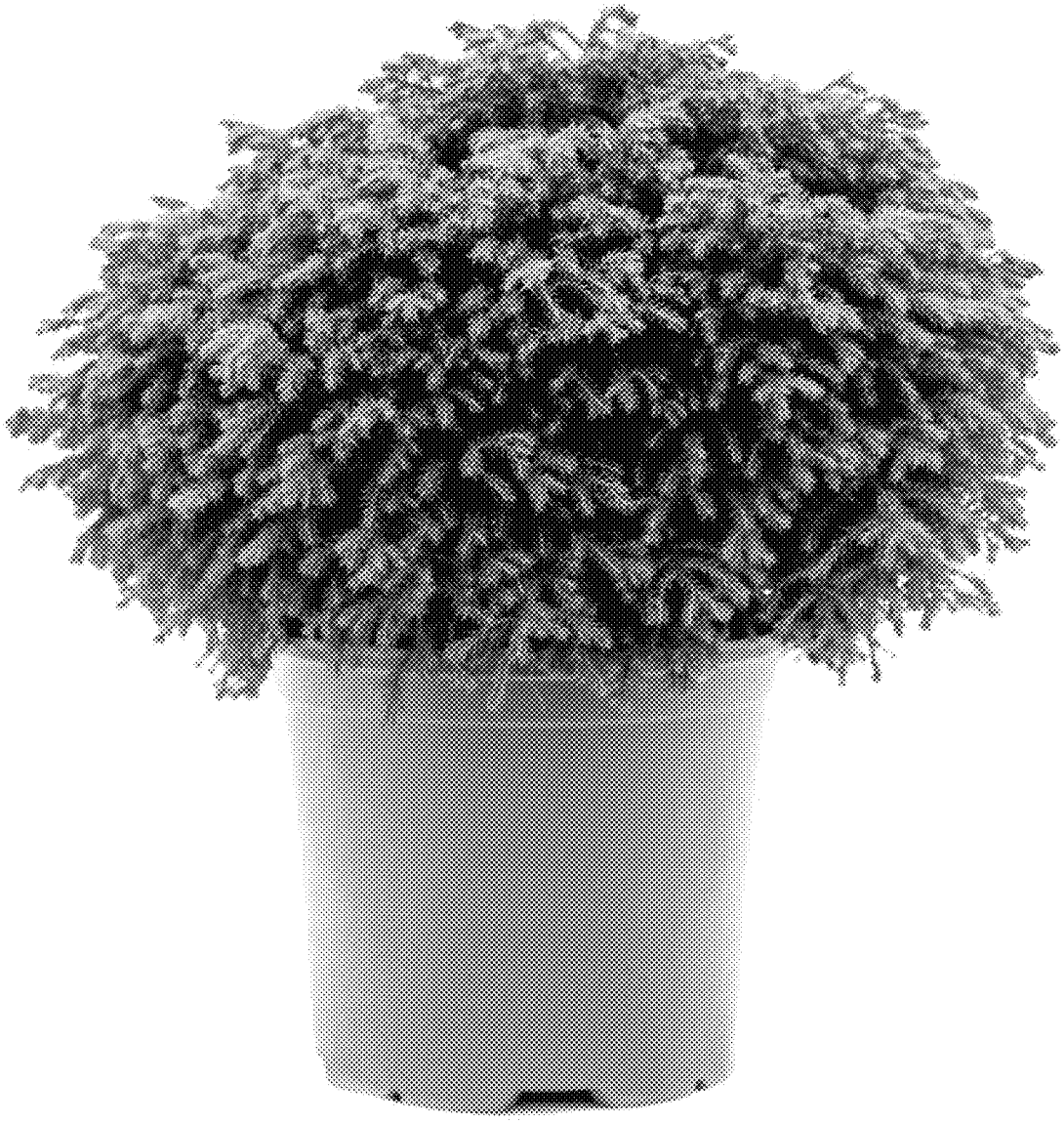

* * * * *